United States Patent
Kalum et al.

(10) Patent No.: US 9,222,078 B2
(45) Date of Patent: Dec. 29, 2015

(54) BLEACHING OF PULP

(75) Inventors: Lisbeth Kalum, Vaerloese (DK); Henrik Lund, Vaerloese (DK); Lars Henrik Oestergaard, Charlottenlund (DK); Hanne Lyngby Hoest Pedersen, Stenloese (DK)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

(21) Appl. No.: 13/805,998

(22) PCT Filed: Jul. 1, 2011

(86) PCT No.: PCT/EP2011/061111
§ 371 (c)(1),
(2), (4) Date: Dec. 20, 2012

(87) PCT Pub. No.: WO2012/001145
PCT Pub. Date: Jan. 5, 2012

(65) Prior Publication Data
US 2013/0098570 A1    Apr. 25, 2013

Related U.S. Application Data

(60) Provisional application No. 61/360,961, filed on Jul. 2, 2010.

(30) Foreign Application Priority Data

Jul. 1, 2010    (EP) .................................... 10168194

(51) Int. Cl.
| | | |
|---|---|---|
| *D21C 9/10* | (2006.01) | |
| *D21C 9/16* | (2006.01) | |
| *C12N 9/08* | (2006.01) | |
| *D21C 5/00* | (2006.01) | |

(52) U.S. Cl.
CPC ............ *C12N 9/0065* (2013.01); *D21C 9/1036* (2013.01); *D21C 5/005* (2013.01); *D21C 9/163* (2013.01)

(58) Field of Classification Search
CPC .......... D21C 5/005; D21C 9/16; D21C 9/163; D21C 9/166; D21H 17/005
USPC ...................................................... 162/72, 78
See application file for complete search history.

(56) References Cited

U.S. PATENT DOCUMENTS

| | | | |
|---|---|---|---|
| 5,691,193 A * | 11/1997 | Paice et al. ..................... 435/278 |
| 6,187,170 B1 | 2/2001 | Hampp | |
| 6,242,245 B1 | 6/2001 | Amann | |
| 6,660,128 B1 | 12/2003 | Bourbonnais | |
| 2006/0054290 A1* | 3/2006 | Call ................................. 162/1 |
| 2008/0190573 A1* | 8/2008 | Xu et al. ......................... 162/73 |

FOREIGN PATENT DOCUMENTS

| | | |
|---|---|---|
| WO | 94-29425 A2 | 12/1994 |
| WO | WO 9510602 A1 * | 4/1995 |
| WO | 97/36039 A1 | 10/1997 |
| WO | 99-54545 A1 | 10/1999 |
| WO | 03-023134 A1 | 3/2003 |
| WO | 2009-069143 A2 | 6/2009 |

OTHER PUBLICATIONS

Espacenet, English Machine Translation of WO 9736039 A1, Oct. 1997.*
Gencore sequence search, SEQ. 1, US-13-805-998-1, Feb. 6, 2014.*
Nielsen et al., Differential Activity and Structure of Highly Similar Peroxidases. Spectroscopic, Crystallographic, and Enzymatic Analyses of Lignifying Arabidopsis thaliana Peroxidase A2 and Horseradish Peroxidase A2, 2001, Biochemistry, 40, p. 11013-11021.*
Gencore Uniprot search of Seq ID #2, Feb. 7, 2014.*
Camarero et al 2004, Enzy Micorbiol Tech 35,113-120.
Gutierrez et al 2009, Appl Microbiol Biotechnol 82, 1005-1018.

* cited by examiner

*Primary Examiner* — Anthony Calandra
(74) *Attorney, Agent, or Firm* — Michael W. Krenicky

(57) ABSTRACT

The use of a peroxidase and violuric acid, or a derivative thereof in the bleaching of pulp, such as paper materials, such as paper, linerboard, corrugated paperboard, tissue, towels, corrugated containers and boxes. The peroxidases of the invention are classified as EC 1.11.1.7. The effect of peroxidase is bleaching and de-inking of the pulp, e.g. the paper pulp and the resulting paper material.

13 Claims, No Drawings

BLEACHING OF PULP

CROSS-REFERENCE TO RELATED APPLICATIONS

This application is a 35 U.S.C. 371 national application of PCT/EP2011/061111 filed Jul. 1, 2011, which claims priority or the benefit under 35 U.S.C. 119 of European application no. 10168194.8 filed Jul. 1, 2010 and U.S. provisional application No. 61/360,961 filed Jul. 2, 2010, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

1. Field of the Invention

The present invention relates to bleaching of pulp with a peroxidase, hydrogen peroxide, and violuric acid or a derivative thereof.

2. Description of the Related Art

It is well-known to use enzymes in the manufacture of paper materials. Examples of enzymes used for this purpose are proteases, lipases, xylanases, amylases, cellulases, as well as various oxidizing enzymes such as laccases and peroxidases.

The effects of these enzymes are wide-spread, e.g. control of various deposits such as pitch, strength-improvement, de-inking, drainage improvement, tissue softening, bleaching etc.

SUMMARY OF THE INVENTION

The present inventors surprisingly found that lignocellulosic materials (e.g. pulp and the resulting paper material) can be bleached efficiently by contacting the lignocellulosic material at about pH 2 to about pH 7 with a peroxidase classified in EC 1.11.1.7, a source of hydrogen peroxide and a mediator selected from violuric acid and certain derivatives thereof.

DETAILED DESCRIPTION OF THE INVENTION

Paper and Pulp

The term "paper material" refers to products, which can be made out of pulp, such as paper, linerboard, corrugated paperboard, tissue, towels, packaging materials, corrugated containers or boxes.

The term "pulp" means any pulp which can be used for the production of a paper material. For example, the pulp can be supplied as a virgin pulp, or can be derived from a recycled source. The pulp may be a wood pulp, a non-wood pulp or a pulp made from waste paper. A wood pulp may be made from softwood such as pine, redwood, fir, spruce, cedar and hemlock or from hardwood such as maple, alder, birch, hickory, beech, aspen, acacia and eucalyptus. A non-wood pulp may be made, e.g., from flax, hemp, bagasse, bamboo, cotton or kenaf. A waste paper pulp may be made by re-pulping waste paper such as newspaper, mixed office waste, computer printout, white ledger, magazines, milk cartons, paper cups etc.

In a particular embodiment, the pulp to be treated comprises both hardwood pulp and softwood pulp.

The wood pulp to be treated may be mechanical pulp (such as ground wood pulp, GP), chemical pulp (such as Kraft pulp or sulfite pulp), semichemical pulp (SCP), thermomechanical pulp (TMP), chemithermomechanical pulp (CTMP), or bleached chemithermomechanical pulp (BCTMP).

Mechanical pulp is manufactured by the grinding and refining methods, wherein the raw material is subjected to periodical pressure impulses. TMP is thermomechanical pulp, GW is groundwood pulp, PGW is pressurized groundwood pulp, RMP is refiner mechanical pulp, PRMP is pressurized refiner mechanical pulp and CTMP is chemithermimechanical pulp.

Chemical pulp is manufactured by alkaline cooking whereby most of the lignin and hemicellulose components are removed. In Kraft pulping or sulphate cooking sodium sulphide or sodium hydroxide are used as principal cooking chemicals.

The Kraft pulp to be treated may be a bleached Kraft pulp, which may consist of softwood bleached Kraft (SWBK, also called NBKP (Nadel Holz Bleached Kraft Pulp)), hardwood bleached Kraft (HWBK, also called LBKP (Laub Holz Bleached Kraft Pulp and)) or a mixture of these.

The pulp to be used in the process of the invention is a suspension of mechanical or chemical pulp or a combination thereof. For example, the pulp to be used in the process of the invention may comprise 0%, 10-20%, 20-30%, 30-40%, 40-50%, 50-60%, 60-70%, 70-80%, 80-90%, or 90-100% of chemical pulp. In a particular embodiment, a chemical pulp forms part of the pulp being used for manufacturing the paper material. In the present context, the expression "forms part of" means that in the pulp to be used in the process of the invention, the percentage of chemical pulp lies within the range of 1-99%. In particular embodiments, the percentage of chemical pulp lies within the range of 2-98%, 3-97%, 4-96%, 5-95%, 6-94%, 7-93%, 8-92%, 9-91%, 10-90%, 15-85%, 20-80%, 25-75%, 30-70%, 40-60%, or 45-55%.

In a particular embodiment of the use and the process of the invention, the chemical pulp is a Kraft pulp, a sulfite pulp, a semichemical pulp (SCP), a thermomechanical pulp (TMP), a chemithermomechanical pulp (CTMP), a bleached chemithermomechanical pulp (BCTMP). In particular embodiments the Kraft pulp is bleached Kraft pulp, for example softwood bleached Kraft (SWBK, also called NBKP (Nadel Holz Bleached Kraft Pulp)), hardwood bleached Kraft (HWBK, also called LBKP (Laub Holz Bleached Kraft Pulp and)) or a mixture thereof.

Bleaching

Bleaching is defined as a process aimed at removal of colour in pulps derived from residual lignin or other colored impurities. Native wood is only slightly colored, whereas residual lignin of a chemical pulp after cooking is highly colored. Traditional concepts for bleaching of pulp includes chlorine and oxygen based oxidants which selectively remove chromophore structures present in the pulp. The progress in bleaching is followed by measuring the brightness, which is defined as the reflectance of visible blue light from a pad of pulp sheets using a defined spectral band of light having an effective wavelength of 457 nm. Official ISO standard methods are ISO 2469 or ISO 2470. Bleaching to full brightness (>88% ISO) requires multi-stage application of bleaching chemicals. The first stages in a bleaching sequence are often conceived as delignification, where the majority of residual lignin is removed. The latter stages are often referred to as brightening stages, in which the chromophores in the pulps are eliminated to attain a high brightness level.

Removal of Lipophilic Extractives

Lipophilic extractives, i.e., the non-polar extractable fraction from wood and other lignocellulosic materials often referred to as wood resin, includes alkanes, fatty alcohols, fatty acids, resin acids, sterols, other terpenoids, conjugated sterols, triglycerides and waxes. These lipophilic compounds cause the so-called pitch deposits along the pulp and paper manufacturing processes. Pitch deposition is a serious problem in the pulp and paper industry since it is responsible for reduced production levels, higher equipment maintenance costs, higher operating costs, and an increased incidence of defects in the finished products, which reduces quality and benefits. Furthermore, process effluents containing wood extractives may be toxic and harmful to the environment.

In addition to bleaching of pulp, the compositions and methods of the invention can also be used for the removal of lipophilic extractives in pulp.

Compositions, Methods and Uses

The present invention provides a method for bleaching pulp, comprising contacting the pulp in an aqueous solution at from about pH 2 to about pH 7 (preferably from about pH 3 to about pH 7, more preferably from about pH 3.5 to about pH 7) with a peroxidase classified in EC 1.11.1.7, a source of hydrogen peroxide, and a mediator having the chemical structure:

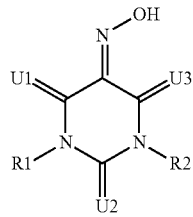

wherein U1, U2 and U3 are identical or different, and are O, S or NOH; and R1 and R2 are identical or different, and are hydrogen, hydroxyl, formyl, carbamoyl or sulfono radical, ester or salt of the sulfono radical, sulfamoyl, nitro, nitroso, amino, cyano, phenyl, benzyl $C_1$-$C_4$-alkyl, $C_1$-$C_4$-alkoxy, $C_1$-$C_4$-carbonyl, or carbonyl-$C_1$-$C_4$-alkyl.

The present invention also provides a method for removal of lipophilic extractives in pulp, comprising contacting the pulp in an aqueous solution at from about pH 2 to about pH 7 (preferably from about pH 3 to about pH 7, more preferably from about pH 3.5 to about pH 7) with a peroxidase classified in EC 1.11.1.7, a source of hydrogen peroxide, and a mediator having the chemical structure:

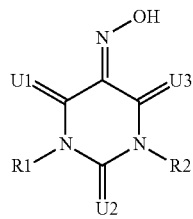

wherein U1, U2 and U3 are identical or different, and are O, S or NOH; and R1 and R2 are identical or different, and are hydrogen, hydroxyl, formyl, carbamoyl or sulfono radical, ester or salt of the sulfono radical, sulfamoyl, nitro, nitroso, amino, cyano, phenyl, benzyl $C_1$-$C_4$-alkyl, $C_1$-$C_4$-alkoxy, $C_1$-$C_4$-carbonyl, or carbonyl-$C_1$-$C_4$-alkyl.

The invention also provides a bleaching composition, comprising a peroxidase classified in EC 1.11.1.7, a source of hydrogen peroxide, and a mediator having the chemical structure:

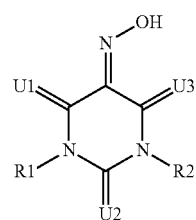

wherein U1, U2 and U3 are identical or different, and are O, S or NOH; and R1 and R2 are identical or different, and are hydrogen, hydroxyl, formyl, carbamoyl or sulfono radical, ester or salt of the sulfono radical, sulfamoyl, nitro, nitroso, amino, cyano, phenyl, benzyl $C_1$-$C_4$-alkyl, $C_1$-$C_4$-alkoxy, $C_1$-$C_4$-carbonyl, or carbonyl-$C_1$-$C_4$-alkyl.

As described above, the composition of the invention can be used for bleaching pulp or for removing lipophilic extractives in pulp.

Preferably, U1, U2 and U3 are identical or different, and are O or S; and R1 and R2 are identical or different, and are hydrogen, hydroxyl, methyl, ethyl, phenyl, benzyl, formyl, amino, cyano, nitroso, methoxy and/or ethoxy.

More preferably, U1, U2 and U3 are O; and R1 and R2 are identical or different, and are hydrogen, hydroxyl, formyl, carbamoyl or sulfono radical, ester or salt of the sulfono radical, sulfamoyl, nitro, nitroso, amino, cyano, phenyl, $C_1$-$C_4$-alkyl, $C_1$-$C_4$-alkoxy, $C_1$-$C_4$-carbonyl, or carbonyl-$C_1$-$C_4$-alkyl.

Most preferably, U1, U2 and U3 are O; and R1 and R2 are identical or different, and are hydrogen, hydroxyl, methyl, ethyl, phenyl, benzyl, formyl, amino, cyano, nitroso, methoxy and/or ethoxy.

In particular, the mediator is selected from 1-methylvioluric acid, 1,3-dimethylvioluric acid, thiovioluric acid, violuric acid, and esters, ethers or salts thereof. More in particular, the mediator is violuric acid, or salts thereof.

In an embodiment, the pulp is wood pulp. Other alternative types of pulp are described above.

In another embodiment, the aqueous solution of the method of the invention has a pH of from about 2.5 to about 6, preferably from about pH 3 to about pH 6, more preferably from about pH 3.5 to about pH 6. Other alternative pH ranges are described below.

In another embodiment, the peroxidase comprises or consists of an amino acid sequence which has at least 80% identity to SEQ ID NO:1, SEQ ID NO:2 or SEQ ID NO:3. Other peroxidases classified in EC 1.11.1.7 are described below.

In yet another embodiment, the methods further comprises a step of alkaline peroxide bleaching.

In a preferred embodiment, the composition further comprises pulp. In another preferred embodiment, the composition is an aqueous composition with a pH of from about 2 to about 7, preferably a pH of from about 3 to about 7, more preferably a pH of from about 3.5 to about 7, most preferably a pH of from about 3 to about 6, and in particular a pH of from about 3.5 to about 6; or a pH of from about 2.5 to about 6. Other alternative pH ranges are the same as are applicable to the methods of the invention, and are described below.

Process Conditions

The process of the invention is particularly applicable to the bleaching of pulp in a process for making paper material.

In the case of paper and pulp processing, the process according to the invention can be carried out at any pulp production stage. The enzyme can be added to any holding tank, e.g. to a pulp storing container (storage chest), storage tower, mixing chest or metering chest. The enzyme treatment can be performed before the bleaching of pulp, in connection with the pulp bleaching process or after the bleaching. When carried out in connection with pulp bleaching the enzyme preparation may be added together with bleaching chemicals such as chlorine or chlorine dioxide. Applying oxygen gas, hydrogen peroxide or ozone or combinations thereof may also carry out the bleaching of pulp. The enzyme preparation may also be added together with these substances. Preferably the enzyme preparation is added prior to bleaching. The enzyme can also be added to the circulated process water (white water) originating from bleaching and process water (brown water) originating from the mechanical or chemimechanical pulping process. In a particular embodiment of a Kraft pulping process, the enzyme is added during the brownstock washing.

In the present context, the term "process water" comprises i.a. 1) water added as a raw material to the paper manufacturing process; 2) intermediate water products resulting from any step of the process for manufacturing the paper material; as well as 3) waste water as an output or by-product of the process. In a particular embodiment, the process water is, has been, is being, or is intended for being circulated (re-circulated), i.e. re-used in another step of the process. The term "water" in turn means any aqueous medium, solution, suspension, e.g. ordinary tap water, and tap water in admixture with various additives and adjuvants commonly used in paper manufacturing processes. In a particular embodiment the process water has a low content of solid (dry) matter, e.g. below 20%, 18%, 16%, 14%, 12%, 10%, 8%, 7%, 6%, 5%, 4%, 3%, 20% or below 1% dry matter.

The process of the invention may be carried out at conventional conditions in the paper and pulp processing. The process conditions will be a function of the enzyme(s) applied, the reaction time and the conditions given.

The enzyme of the invention should be added in an effective amount. By the term "effective amount" is meant the amount sufficient to achieve the desired and expected effect, such as oxidizing pitch components, obtaining a desired bleaching and/or de-inking etc.

In a particular embodiment, the dosage of the peroxidase and additional enzymes, if any, is from about 0.1 mg enzyme protein to about 100,000 mg enzyme protein (of each enzyme) per ton of paper pulp.

In further particular embodiments, the amount of the peroxidase and additional enzymes, if any, is in the range of 0.00001-20; or 0.0001-20 mg of enzyme (calculated as pure enzyme protein) per gram (dry weight) of pulp material, such as 0.0001-10 mg/g, 0.0001-1 mg/g, 0.001-1 mg/g, 0.001-0.1, or 0.01-0.1 mg of enzyme per gram of pulp material. Again, these amounts refer to the amount of each enzyme.

The enzymatic treatment can be done at conventional consistency, e.g. 0.5-10% dry substance. In particular embodiments, the consistency is within the range of 0.5-45%; 0.5-40%; 0.5-35%; 0.5-30%; 0.5-25%; 0.5-20%; 0.5-15%; 0.5-10%; 0.5-8%; 0.5-6%; or 0.5-5% dry substance.

The enzymatic treatment may be carried out at a temperature of from about 10° C. to about 100° C. Further examples of temperature ranges (all "from about" and "to about") are the following: 20-120° C., 30-120° C., 35-120° C., 37-120° C., 40-120° C., 50-120° C., 60-120° C., 70-120° C., 10-100° C., 10-90° C., 10-80° C., 10-70° C., 10-60° C., and 30-60° C., as well as any combination of the upper and lower values here indicated. A typical temperature is from about 20 to 90° C., or 20 to 95° C., preferably from about 40 to 70° C., or 40 to 75° C. Usually, the enzymatic treatment is carried out at atmospheric pressure. But when the temperature exceeds 100° C., the treatment is carried out at a pressure of 1-2 bar (up to 1 bar above atmospheric pressure).

The enzymatic treatment is carried out at a pH of from about 2 to about 7, preferably at a pH from about 2.5 to about 6, more preferably at a pH from about 3 to about 5.5, and most preferably at a pH from about 3.5 to about 5.

A suitable duration of the enzymatic treatment may be in the range from a few seconds to several hours, e.g. from about 30 seconds to about 48 hours, or from about 1 minute to about 24 hours, or from about 1 minute to about 18 hours, or from about 1 minute to about 12 hours, or from about 1 minute to 5 hours, or from about 1 minute to about 2 hours, or from about 1 minute to about 1 hour, or from about 1 minute to about 30 minutes. A typical reaction time is from about 10 minutes to 3 hours, 10 minutes to 10 hours, preferably 15 minutes to 1 hour, or 15 minutes to 2 hours.

Molecular oxygen from the atmosphere will usually be present in sufficient quantity, if required. Therefore, the reaction may conveniently be carried out in an open reactor, i.e. at atmospheric pressure.

Various additives over and above the peroxidase and additional enzymes, if any, can be used in the process or use of the invention. Surfactants and/or dispersants are often present in, and/or added to a pulp. Thus the process and use of the present invention may be carried out in the presence of an anionic, non-ionic, cationic and/or zwitterionic surfactant and/or dispersant conventionally used in a pulp. Examples of anionic surfactants are carboxylates, sulphates, sulphonates or phosphates of alkyl, substituted alkyl or aryl. Examples of non-ionic surfactants are polyoxyethylene compounds, such as alcohol ethoxylates, propoxylates or mixed ethoxy-/propoxylates, poly-glycerols and other polyols, as well as certain block-copolymers. Examples of cationic surfactants are water-soluble cationic polymers, such as quartenary ammonium sulphates and certain amines, e.g. epichlorohydrin/dimethylamine polymers (EPI-DMA) and cross-linked solutions thereof, polydiallyl dimethyl ammonium chloride (DADMAC), DADMAC/Acrylamide co-polymers, and ionene polymers, such as those disclosed in U.S. Pat. Nos. 5,681, 862; and 5,575,993. Examples of zwitterionic or amphoteric surfactants are betains, glycinates, amino propionates, imino propionates and various imidazolin-derivatives. Also the polymers disclosed in U.S. Pat. No. 5,256,252 may be used.

Also according to the invention, surfactants such as the above, including any combination thereof may be used in a paper making process together with a peroxidase as defined herein, and included in a composition together with such enzyme. The amount of each surfactant in such composition may amount to from about 1 to about 1000 ppm of the composition. In particular embodiments the amount of each surfactant is from about 10 to about 1000 ppm, or from about 10 to about 500 ppm, or from about 50 to about 500 ppm.

In another particular embodiment, each of the above ranges refers to the total amount of surfactants.

In further particular embodiments of the above method, and of the process of the invention, the peroxidase is used in an amount of 0.005-50 ppm (mg/L), or 0.01-40, 0.02-30, 0.03-25, 0.04-20, 0.05-15, 0.05-10, 0.05-5, 0.05-1, 0.05-0.8, 0.05-0.6, or 0.1-0.5 ppm. The amount of enzyme refers to mg of a well-defined enzyme preparation.

In the process of the invention, the peroxidase may be applied alone or together with an additional enzyme. The term "an additional enzyme" means at least one additional enzyme, e.g. one, two, three, four, five, six, seven, eight, nine, ten or even more additional enzymes.

The term "applied together with" (or "used together with") means that the additional enzyme may be applied in the same, or in another step of the process of the invention. The other process step may be upstream or downstream in the paper manufacturing process, as compared to the step in which the pulp is bleached with a peroxidase.

In particular embodiments the additional enzyme is an enzyme which has protease, lipase, xylanase, cutinase, oxidoreductase, cellulase, endoglucanase, amylase, mannanase, steryl esterase, and/or cholesterol esterase activity. Examples of oxidoreductase enzymes are enzymes with laccase, and/or peroxidase activity. In a preferred embodiment, the additional enzyme is lipase.

The term "a step" of a process means at least one step, and it could be one, two, three, four, five or even more process steps. In other words the peroxidase of the invention may be applied in at least one process step, and the additional enzyme(s) may also be applied in at least one process step, which may be the same or a different process step as compared to the step where the peroxidase is used.

The term "enzyme preparation" means a product containing at least one peroxidase. The enzyme preparation may also comprise enzymes having other enzyme activities, preferably lipolytic enzymes. In addition to the enzymatic activity such a preparation preferably contains at least one adjuvant. Examples of adjuvants, which are used in enzyme preparations for the paper and pulp industry are buffers, polymers, surfactants and stabilizing agents.

In an embodiment, the process of the invention also includes an alkaline peroxide bleaching stage (E stage and/or P stage), such as described by Camarero, S. et al., Enzyme and Microbial Technology, 35 (2004), pp. 113-120 (see in particular paragraph 2.4). Preferably, the alkaline peroxide bleaching is carried out after the enzymatic bleaching method of the invention. Typical conditions for an alkaline peroxide bleaching stage are initial pH values in the range of 10-11 and end pH above 8.5; temperatures typical ranges from 70-90° C. and peroxide charges from 0.5-1% for 1.5 hours. Peroxide stabilizer may be added and metal management may be handled in previous stage or simultaneously with peroxide bleaching.

Peroxidase Enzymes

EC-numbers may be used for classification of enzymes. Reference is made to the Recommendations of the Nomenclature Committee of the International Union of Biochemistry and Molecular Biology, Academic Press Inc., 1992.

It is to be understood that the term enzyme, as well as the various enzymes and enzyme classes mentioned herein, encompass wild-type enzymes, as well as any variant thereof that retains the activity in question. Such variants may be produced by recombinant techniques.

The wild-type enzymes may also be produced by recombinant techniques, or by isolation and purification from the natural source.

In a particular embodiment the enzyme in question is well-defined, meaning that only one major enzyme component is present. This can be inferred e.g. by fractionation on an appropriate size-exclusion column. Such well-defined, or purified, or highly purified, enzyme can be obtained as is known in the art and/or described in publications relating to the specific enzyme in question.

A peroxidase according to the invention is a peroxidase enzyme comprised by the enzyme classification EC 1.11.1.7, or any fragment derived therefrom, exhibiting peroxidase activity.

Preferably, the peroxidase according of the invention is a plant peroxidase (e.g. horseradish peroxidase (see SEQ ID NO:2), soybean peroxidase (see SEQ ID NO:3), or royal palm tree peroxidase (see SEQ ID NO:4)), or a fungal or bacterial peroxidase.

Some preferred fungi include strains belonging to the subdivision Deuteromycotina, class Hyphomycetes, e.g., *Fusarium, Humicola, Tricoderma, Myrothecium, Verticillum, Arthromyces, Caldariomyces, Ulocladium, Embellisia, Cladosporium* or *Dreschlera*, in particular *Fusarium oxysporum* (DSM 2672), *Humicola insolens, Trichoderma resii, Myrothecium verrucaria* (IFO 6113), *Verticillum alboatrum, Verticillum dahlie, Arthromyces ramosus* (FERM P-7754), *Caldariomyces fumago, Ulocladium chartarum, Embellisia alli* or *Dreschlera halodes*.

Other preferred fungi include strains belonging to the subdivision Basidiomycotina, class Basidiomycetes, e.g., *Coprinus, Phanerochaete, Coriolus* or *Trametes*, in particular *Coprinus cinereus* f. *microsporus* (IFO 8371), *Coprinus macrorhizus, Phanerochaete chrysosporium* (e.g. NA-12) or *Trametes* (previously called *Polyporus*), e.g., *T. versicolor* (e.g. PR428-A).

Further preferred fungi include strains belonging to the subdivision Zygomycotina, class Mycoraceae, e.g., *Rhizopus* or *Mucor*, in particular *Mucor hiemalis*.

Some preferred bacteria include strains of the order Actinomycetales, e.g. *Streptomyces spheroides* (ATTC 23965), *Streptomyces thermoviolaceus* (IFO 12382) or *Streptoverticillum verticillium* ssp. *verticillium*.

Other preferred bacteria include *Rhodobacter sphaeroides, Rhodomonas palustri, Streptococcus lactis, Pseudomonas purrocinia* (ATCC 15958), *Pseudomonas fluorescens* (NRRL B-11) and *Bacillus* strains, e.g. *Bacillus pumilus* (ATCC 12905) and *Bacillus stearothermophilus*.

Further preferred bacteria include strains belonging to *Myxococcus*, e.g., *M. virescens*.

The peroxidase may furthermore be one which is producible by a method comprising cultivating a host cell transformed with a recombinant DNA vector which carries a DNA sequence encoding said peroxidase as well as DNA sequences encoding functions permitting the expression of the DNA sequence encoding the peroxidase, in a culture medium under conditions permitting the expression of the peroxidase and recovering the peroxidase from the culture.

Particularly, a recombinantly produced peroxidase is a peroxidase derived from a *Coprinus* sp. (also referred to as *Coprinopsis* sp.), in particular *C. macrorhizus* or *C. cinereus* (see e.g. SEQ ID NO:1).

In a preferred embodiment, the peroxidase of the methods and compositions of the invention comprises an amino acid sequence which has at least 80% identity, such as at least 85% identity, at least 90% identity or at least 95% identity, to SEQ ID NO:1, SEQ ID NO:2, SEQ ID NO:3, or SEQ ID NO:4.

In another preferred embodiment, the peroxidase of the methods and compositions of the invention consists of an amino acid sequence which has at least 80% identity, such as at least 85% identity, at least 90% identity or at least 95% identity, to SEQ ID NO:1, SEQ ID NO:2, SEQ ID NO:3, or SEQ ID NO:4.

In another preferred embodiment, the peroxidase of the methods and compositions of the invention comprises or consists of an amino acid sequence which has one or several (such as 1-10 or 1-5) amino acid substitutions compared to the amino acid sequence of SEQ ID NO:1, SEQ ID NO:2, SEQ ID NO:3, or SEQ ID NO:4.

In another preferred embodiment, the peroxidase of the methods and compositions of the invention comprises an amino acid sequence selected from the group consisting of the amino acid sequence of SEQ ID NO:1, SEQ ID NO:2, SEQ ID NO:3, and SEQ ID NO:4.

In another preferred embodiment, the peroxidase of the methods and compositions of the invention consists of an amino acid sequence selected from the group consisting of the amino acid sequence of SEQ ID NO:1, SEQ ID NO:2, SEQ ID NO:3, and SEQ ID NO:4.

In the context of this invention, compounds possessing peroxidase activity comprise peroxidase enzymes and peroxidase active fragments derived from cytochromes, haemoglobin or peroxidase enzymes.

Determination of Peroxidase Activity (PDXU)

One peroxidase unit (PDXU) is the amount of enzyme which catalyze the conversion of one µmole hydrogen peroxide per minute at 30° C. in a mixture containing:
0.1 M phosphate buffer, pH 7.0;
0.88 mM hydrogen peroxide; and
1.67 mM 2,2'-azino-bis(3-ethylbenzothiazoline-6-sulfonate) (ABTS).

The reaction is continued for 60 seconds (15 seconds after mixing) while the change in absorbance at 418 nm is measured. The absorbance should be in the range of 0.15 to 0.30. Peroxidase activity is calculated using an absorption coefficient of oxidized ABTS of 36 mM$^{-1}$ cm$^{-1}$, and a stoichiometry of one µmole $H_2O_2$ converted per two µmole ABTS oxidized.

Source of Hydrogen Peroxide

The source of hydrogen peroxide required by the peroxidase, or compounds exhibiting peroxidase activity, may be provided as an aqueous solution of hydrogen peroxide or a hydrogen peroxide precursor for in situ production of hydrogen peroxide. Any solid entity which liberates upon dissolution a peroxide which is useable by peroxidase can serve as a source of hydrogen peroxide. Compounds which yield hydrogen peroxide upon dissolution in water or an appropriate aqueous based medium include but are not limited to metal peroxides, percarbonates, persulphates, perphosphates, peroxyacids, alkyperoxides, acylperoxides, peroxyesters, urea peroxide, perborates and peroxycarboxylic acids or salts thereof.

Another source of hydrogen peroxide is a hydrogen peroxide generating enzyme system, such as an oxidase together with a substrate for the oxidase. Examples of combinations of oxidase and substrate comprise, but are not limited to, amino acid oxidase (see e.g. U.S. Pat. No. 6,248,575) and a suitable amino acid, glucose oxidase (see e.g. WO 95/29996) and glucose, lactate oxidase and lactate, galactose oxidase (see e.g. WO 00/50606) and galactose, and aldose oxidase (see e.g. WO 99/31990) and a suitable aldose.

By studying EC 1.1.3.-, EC 1.2.3.-, EC 1.4.3.-, and EC 1.5.3.- or similar classes (under the International Union of Biochemistry), other examples of such combinations of oxidases and substrates are easily recognized by one skilled in the art.

Hydrogen peroxide or a source of hydrogen peroxide may be added at the beginning of or during the process, e.g., typically in an amount corresponding to levels of from 0.001 mM to 25 mM, preferably to levels of from 0.005 mM to 5 mM, and particularly to levels of from 0.01 to 1 mM hydrogen peroxide. Hydrogen peroxide may also be used in an amount corresponding to levels of from 0.1 mM to 25 mM, preferably to levels of from 0.5 mM to 15 mM, more preferably to levels of from 1 mM to 10 mM, and most preferably to levels of from 2 mM to 8 mM hydrogen peroxide.

Mediator

The mediators according to the invention act as electron donors for the peroxidase. The mediator compounds improve the electron transfer between the peroxidase and the pulp to improve the bleaching effect of the methods of the invention. The mediators according to the invention have the chemical structure:

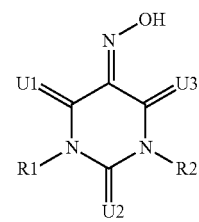

wherein U1, U2 and U3 are identical or different, and are O, S or NOH; and R1 and R2 are identical or different, and are hydrogen, hydroxyl, formyl, carbamoyl or sulfono radical, ester or salt of the sulfono radical, sulfamoyl, nitro, nitroso, amino, cyano, phenyl, benzyl, $C_1$-$C_4$-alkyl, $C_1$-$C_4$-alkoxy, $C_1$-$C_4$-carbonyl, carbonyl-$C_1$-$C_4$-alkyl.

In an embodiment, U1, U2 and U3 are identical or different, and are O or S; and R1 and R2 are identical or different, and are hydrogen, hydroxyl, formyl, carbamoyl or sulfono radical, ester or salt of the sulfono radical, sulfamoyl, nitro, nitroso, amino, cyano, phenyl, benzyl, $C_1$-$C_4$-alkyl, $C_1$-$C_4$-alkoxy, $C_1$-$C_4$-carbonyl, carbonyl-$C_1$-$C_4$-alkyl.

In another embodiment, U1, U2 and U3 are O; and R1 and R2 are identical or different, and are hydrogen, hydroxyl, formyl, carbamoyl or sulfono radical, ester or salt of the sulfono radical, sulfamoyl, nitro, nitroso, amino, cyano, phenyl, benzyl, $C_1$-$C_4$-alkyl, $C_1$-$C_4$-alkoxy, $C_1$-$C_4$-carbonyl, carbonyl-$C_1$-$C_4$-alkyl.

In another embodiment, U1, U2 and U3 are identical or different, and are O, S or NOH; and R1 and R2 are identical or different, and are hydrogen, hydroxyl, methyl, ethyl, phenyl, benzyl, formyl, amino, cyano, nitroso, methoxy and/or ethoxy.

In another embodiment, U1, U2 and U3 are identical or different, and are O or S; and R1 and R2 are identical or different, and are hydrogen, hydroxyl, methyl, ethyl, phenyl, benzyl, formyl, amino, cyano, nitroso, methoxy and/or ethoxy.

In another embodiment, U1, U2 and U3 are O; and R1 and R2 are identical or different, and are hydrogen, hydroxyl, methyl, ethyl, phenyl, benzyl, formyl, amino, cyano, nitroso, methoxy and/or ethoxy.

Preferred mediators are 1-methylvioluric acid, 1,3-dimethylvioluric acid, thiovioluric acid and violuric acid (alloxan-4,5-dioxime).

A particularly preferred mediator is alloxan-5-oxime (violuric acid) and/or its esters, ethers or salts.

According to the invention, the mediator may be present in a concentration in the range of from 0.01 mM to 1000 mM, preferably in the range of from 0.05 mM to 500 mM, more preferably in the range of from 0.05 mM to 100 mM, and most preferably in the range of from 0.1 mM to 50 mM.

Additional Enzymes

Any enzyme having protease, lipase, xylanase, cutinase, oxidoreductase, cellulase endoglucanase, amylase, mannanase, steryl esterase, and/or cholesterol esterase activity can be used as additional enzymes in the use and process of the invention. Below some non-limiting examples are listed of such additional enzymes. The enzymes written in capitals are commercial enzymes available from Novozymes NS, Krogshoejvej 36, DK-2880 Bagsvaerd, Denmark. The activity of any of those additional enzymes can be analyzed using any method known in the art for the enzyme in question, including the methods mentioned in the references cited.

Examples of cutinases are those derived from *Humicola insolens* (U.S. Pat. No. 5,827,719); from a strain of *Fusarium*, e.g. *F. roseum culmorum*, or particularly *F. solani pisi* (WO 90/09446; WO 94/14964, WO 94/03578). The cutinase may also be derived from a strain of *Rhizoctonia*, e.g. *R. solani*, or a strain of *Alternaria*, e.g. *A. brassicicola* (WO 94/03578), or variants thereof such as those described in WO 00/34450, or WO 01/92502.

Examples of proteases are the ALCALASE, ESPERASE, SAVINASE, NEUTRASE and DURAZYM proteases. Other proteases are derived from *Nocardiopsis, Aspergillus, Rhizopus, Bacillus alcalophilus, B. cereus, B. natto, B. vulgatus, B. mycoide*, and *subtilisins* from *Bacillus*, especially proteases from the species *Nocardiopsis* sp. and *Nocardiopsis dassonvillei* such as those disclosed in WO 88/03947, and mutants thereof, e.g. those disclosed in WO 91/00345 and EP 415296.

Examples of amylases are the BAN, AQUAZYM, TERMAMYL, and AQUAZYM Ultra amylases. An example of a lipase is the RESINASE A2X lipase. An example of a xylanase is the PULPZYME HC hemicellulase. Examples of endoglucanases are the NOVOZYM 613, 342, and 476 enzyme products.

Examples of mannanases are the *Trichoderma reesei* endo-beta-mannanases described in Ståhlbrand et al, J. Biotechnol. 29 (1993), 229-242.

Examples of steryl esterases. peroxidases, laccases, and cholesterol esterases are disclosed in the references mentioned in the background art section hereof. Further examples of oxidoreductases are the peroxidases and laccases disclosed in EP 730641; WO 01/98469; EP 719337; EP 765394; EP 767836; EP 763115; and EP 788547. In the present context, whenever an oxidoreductase enzyme is mentioned that requires or benefits from the presence of acceptors (e.g. oxygen or hydrogenperoxide), enhancers, mediators and/or activators, such compounds should be considered to be included. Examples of enhancers and mediators are disclosed in EP 705327; WO 98/56899; EP 677102; EP 781328; and EP 707637. If desired a distinction could be made by defining an oxidoreductase enzyme system (e.g. a laccase, or a peroxidase enzyme system) as the combination of the enzyme in question and its acceptor, and optionally also an enhancer and/or mediator for the enzyme in question.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

EXAMPLES

The amino acid sequence of *Coprinus cinereus* peroxidase (CiP) is shown as SEQ ID NO:1.
The amino acid sequence of horseradish peroxidase (HRP) is shown as SEQ ID NO:2.
The amino acid sequence of soybean peroxidase (SBP) is shown as SEQ ID NO:3.
The amino acid sequence of royal palm tree peroxidase (RPP) is shown as SEQ ID NO:4.
The amino acid sequence of *Polyporus pinsitus* laccase (PpL) is shown in WO 96/00290, FIG. 1, sequence number 1.
The amino acid sequence of *Coprinus cinereus* laccase (CcL) is shown in WO 97/08325, FIG. 1, sequence number 27.

Standard Laboratory Protocol for Mini Pulp Assay 60 mg dry unbleached pulp is weighed into 10 mL glass tubes. Typically 12-40 tubes are prepared per trial. 2 mL buffer solution is added to each tube and the pulp is left to pre-soak for 30 minutes at room temperature. Enzyme solution is added in order to reach the desired concentration. A magnet (e.g. 4.5×15 mm) is added to each tube. The tubes is placed in a stirring block thermostat (Variomag Themomodul 40ST with 50 wholes) preheated to the desired temperature (e.g. 40-50° C.). After approx. 5 minutes the mediator stock solution and other auxiliaries are added. Deionized water is added to reach a final liquid volume of 4 mL and the pulp suspension is thoroughly mixed. Oxidant is added. When evaluating peroxidases, the oxidant is hydrogen peroxide added as 2×2 mM hydrogen peroxide, where second hydrogen peroxide addition is after 30 minutes incubation. The oxidant for laccases is molecular oxygen supplied through a small plastic tube providing a constant flow of oxygen from the bottom of the pulp suspension. The samples are incubated for 60 minutes under magnetic stirring using the stirring block thermostat at the desired temperature. After the enzyme mediator incubation, the magnet is removed and the tubes are centrifuged for 5 minutes at 4000 rpm using an Eppendorf Centrifuge 5810. The supernatant is removed by decanting and the pulp is re-suspended in 6 mL deionized water. This washing procedure is repeated—centrifugation, re-suspension in 6 mL deionzied and centrifugation. The washed pulp is treated with 2 mL alkaline solution containing 0.5 g/L EDTA, 2.0 g/L NaOH and 1 g/L $H_2O_2$. The alkaline suspension is placed in a water bath for 30 min at 80° C. with no stirring. Subsequently, the tubes are centrifuged for 5 minutes at 4000 rpm using an Eppendorf Centrifuge 5810 and the supernatant removed by decanting. The pulp is re-suspended in 8 mL deionized water and filtered through a nylon filter (diameter 20 mm) under suction. The formed paper pads are placed on a metal plate, covered with 3 layers of filter paper and pressed in a two step procedure using a Labtech automatic sheet press. Press step 1: 0.4 MPa for 5.5 minutes and press step 2: 0.4 MPa for 3 minutes. The pads are dried over night at room temperature. Brightness is determined using a Macbeth Color-Eye 7000 Remissions spectrophotometer, measuring two times on each pad at 460 nm (on each side).

Example 1

Bleaching of Flax Pulp with *Coprinus cinereus* Peroxidase and Violuric Acid

*Coprinus cinereus* peroxidase (CiP) was evaluated on unbleached flax pulp using violuric acid (VA; Fluka 95120) as mediator. The standard laboratory protocol for the mini assay was applied, and the flax pulp was hydrated and disintegrated in buffer for approx. 18 hours at 50° C. under magnetic stirring. The CiP-VA system was compared to three laccase mediator system:
*Polyporus* pinsitus laccase (PpL) and 1-hydroxy-benzotriazole (HOBT);
*Polyporus* pinsitus laccase and violuric acid (VA);
*Coprinus cinereus* laccase (CcL) and violuric acid.
The brightness of the original pulp sheet prior to disintegration is listed as market pulp.

Conditions:
0.01 mg peroxidase protein/mL;
0.1 g/L Neodol 25-3 (surfactant);
50° C.;
pH as stated in Table 1;
mediator concentrations as stated in Table 1.

The brightness values were based on double determinations. A stock solution of mediator was prepared prior to addition: violuric acid was dissolved in de-ionized water; and HOBT was dissolved in ethanol and diluted in de-ionized water.

TABLE 1

Brightness of unbleached flax pulp after treatment with oxidase-mediator systems as described in the standard laboratory protocol.

|  | CiP-VA pH 5 | PpL-VA pH 4 | PpL-HOBT pH 4 | CcL-VA pH 6 |
|---|---|---|---|---|
| Market pulp |  | 40.6 |  |  |
| Blank | 54.6 | 54.9 | 54.9 | 54.3 |
| Control | 59.9 | 57.9 | 57.9 | 55.4 |
| 1 mM mediator | 70.5 | 66.9 | 67.8 | 61.0 |
| 3 mM mediator | 73.6 | 68.2 | 70.0 | 62.8 |
| 5 mM mediator | 73.9 | 68.4 | ND | 64.3 |

The combination of CiP and VA was more efficient than the laccase/mediator systems evaluated.

Example 2

Bleaching of Eucalyptus Pulp with *Coprinus cinereus* Peroxidase and Violuric Acid The CiP-VA system was applied to bleach Eucalyptus pulp using the standard laboratory protocol for mini pulp assay. The pulp was hydrated in 50 mM acetate buffer pH 4.5 for 30 minutes at room temperature. Four mediator concentrations were tested. Brightness of the formed paper pads was measured and the result shown in Table 2.
Conditions:
0.01 mg peroxidase protein/mL;
0.1 g/L Neodol 25-3 (surfactant);
50° C.;
pH 4.5;
mediator concentrations as stated in Table 2.
2×2 mM hydrogen peroxide added as indicated in the Table 2.

The brightness values were based on double determinations.

TABLE 2

Brightness of unbleached Eucalyptus pulp after treatment with CiP-VA system as described in the standard laboratory protocol. No hydrogen peroxide and surfactant were added to the blank treatment.

| Treatment | Brightness |
|---|---|
| Blank | 42.9 |
| $H_2O_2$ + surfactant | 44.2 |
| CiP + $H_2O_2$ + surfactant | 44.7 |
| CiP + $H_2O_2$ + surfactant + 1 mM VA | 57.5 |
| CiP + $H_2O_2$ + surfactant + 2 mM VA | 58.9 |
| CiP + $H_2O_2$ + surfactant + 3 mM VA | 60.3 |

Treatment of unbleached eucalyptus pulp with the CiP-VA system resulted in surprisingly high increase in brightness.

Example 3

Bleaching of Pulp with *Coprinus cinereus* Peroxidase and Different Mediators

Performance of the *Coprinus cinereus* peroxidase (CiP) and violuric acid (VA) system on unbleached eucalyptus pulp was compared to other N-hydroxy mediators at equal mediator dose (2 mM). The standard laboratory protocol for the mini assay was applied, and the eucalyptus pulp was hydrated for in 50 mM acetate buffer pH 4.5 for 30 minutes at room temperature (no stirring).
Conditions:
0.001 mg peroxidase protein/mL;
0.1 g/L Neodol 25-3 (surfactant);
50° C.;
pH 4.5;
2 mM mediator as stated in Table 3.
2×2 mM hydrogen peroxide.

The brightness values were based on double determinations. A stock solution of mediator was prepared prior to addition: violuric acid and 4-methoxy-Tempo were dissolved in de-ionized water; and HOBT and N-hydroxyphathalimide were dissolved in ethanol and diluted in de-ionized water.

TABLE 3

Brightness of unbleached Eucalyptus pulp after treatment with CiP-mediator system as described in the standard laboratory protocol. No hydrogen peroxide and surfactant were added to the blank treatment.

| Treatment | Brightness |
|---|---|
| Blank | 42.2 |
| CiP + $H_2O_2$ + surfactant + 2 mM violuric acid | 57.7 |
| CiP + $H_2O_2$ + surfactant + 2 mM 1-hydroxybenzotriazole (HOBT) | 47.1 |
| CiP + $H_2O_2$ + surfactant + 2 mM 4-methoxy-Tempo | 46.5 |
| CiP + $H_2O_2$ + surfactant + 2 mM N-hydroxyphthalimide | 45.3 |

The CiP-VA system was superior to other N-hydroxy mediators.

Example 4

Bleaching of Wood Pulp with *Coprinus cinereus* Peroxidase and Violuric Acid

Unbleached birch pulp and unbleached eucalyptus pulp sampled before and after oxygenation were treated with *Coprinus cinereus* peroxidase (CiP) and violuric acid (VA). Oxygenation is a well established procedure both in ECF and TCF bleaching. The standard laboratory protocol for the mini assay was applied, and the pulps were hydrated for in 50 mM acetate buffer pH 4.5 for 30 minutes at room temperature (no stirring).
Conditions:
0.005 mg peroxidase protein/mL;
0.1 g/L Neodol 25-3 (surfactant);
50° C.;
pH 4.5;
concentration of violuric acid as stated in Table 3;
2×2 mM hydrogen peroxide.

The brightness values were based on double determinations. Violuric acid was added from a stock solution prepared in de-ionized water.

TABLE 4

Brightness of different unbleached hardwood pulps after treatment with CiP-VA system. No hydrogen peroxide and surfactant were added to the blank treatment.

| Pulp | Violuric acid (mM) | Brightness |
|---|---|---|
| Unbleached Eucalyptus | blank | 42.9 |
|  | 0.5 | 55.8 |
|  | 2 | 57.8 |
| Oxygenated Eucalyptus | 0.5 | 62.8 |
|  | 1 | 72.7 |
|  | 5 | 74.4 |
| Birch | 0.5 | 41.1 |
|  | 1 | 51.5 |
|  | 5 | 55.3 |

The CiP-VA system improved brightness significantly on all three types of pulp.

Example 5

Bleaching of Eucalyptus with Plant Peroxidases and Violuric Acid

Unbleached eucalyptus pulp sampled before oxygenation were treated with soybean peroxidase (SBP; Sigma P1432, 90 purpurogallin units/mg; SEQ ID NO:3) and horseradish peroxidase (HRP; Type VI-A, Sigma P6782; 1000 ABTS units/mg; SEQ ID NO:2) and compared to lignin peroxidase (LiP; Sigma 42603, 0.46 U/mg of dimethoxy benzylalcohol) and Coprinus cinereus peroxidase (CiP) and 0.5 mM violuric acid (VA). The standard laboratory protocol for the mini assay was applied, and the pulps were hydrated for in 50 mM acetate buffer pH 4.0 or pH 4.5 for 30 minutes at room temperature (no stirring).

Conditions:

0.001 mg CiP protein/mL; 1.8 ABTS units HRP/ml; 1.8 purpurogallin units SBP/mg; 0.0005 LiP U/ml.

0.1 g/L Neodol 25-3 (surfactant);

40° C.;

pH 4.0 or 4.5;

0.5 mM violuric acid (VA; Fluka 95120)

2×1 mM hydrogen peroxide added as indicated in the Table 5.

The brightness values were based on double determinations. A stock solution of 40 mM violuric acid was prepared de-ionized water.

TABLE 5

Brightness of unbleached eucalyptus kraft pulp after treatment with CiP, LiP, HRP and SBP and 0.5 mM violuric acid. No hydrogen peroxide and surfactant were added to the blank treatment.

| Peroxidase | Conditions | Brightness |
|---|---|---|
| Blank | pH 4.5 buffer | 41.6 |
| Control | pH 4.5 + $H_2O_2$ + surfactant | 44.1 |
| CiP | pH 4.5 + $H_2O_2$ + surfactant + VA | 52.5 |
| LiP | pH 4.0 + $H_2O_2$ + surfactant + VA | 44.9 |
| HRP | pH 4.5 + $H_2O_2$ + surfactant + VA | 48.8 |
| SBP | pH 4.0 + $H_2O_2$ + surfactant + VA | 52.9 |
| SBP | pH 4.5 + $H_2O_2$ + surfactant + VA | 55.5 |

CiP, SBP and HRP all improved brightness of the unbleached eucalyptus kraft pulp.

Example 6

Bleaching of Eucalyptus with CiP at 9% Consistency—Time Profile

Oxygenated eucalyptus pulp was treated with Coprinus cinereus peroxidase (CiP) and 0.5 mM violuric acid (VA; Fluka 95120) for 15, 60 and 240 min at 9% consistency. The following procedure was applied:

2 g dry oxygenated eucalyptus pulp was weighed into a stomacher bag (BA6040, Seward). 10 ml 50 mM acetate buffer pH 4.5 was added to the pulp and the stomacher bag was sealed. The pulp was hydrated for 30 minutes at 45° C. in a water bath. De-ionized water, enzyme, mediator, surfactant and peroxide was added to the pulp (in the stated order) and mixed by hand between each ingredient. The amount of water was adjusted to give a final volume of 20 ml. The actual concentrations in each treatment were as listed in Table 6. The samples were incubated for the designated time and the pulp drained by filtration (vacuum) using a glass funnel with a binding clamp polyester. The drained pulp was washed twice with 40 ml of de-ionized water and drained. The pulp pads were placed on a metal plate, covered with 3 layers of filter paper and pressed in a two step procedure using a Labtech automatic sheet press. Press step 1: 0.4 MPa for 5.5 minutes and press step 2: 0.4 MPa for 3 minutes. The pads were weighed and dry matter content calculated (typically in the range of 50% dry matter). 120 mg semi dry pulp was treated with 2 mL alkaline solution containing 0.5 g/L EDTA, 2.0 g/L NaOH and 1 g/L $H_2O_2$. The alkaline suspension is placed in a water bath for 30 min at 80° C. with no stirring. Subsequently, the tubes were centrifuged for 5 minutes at 4000 rpm using an Eppendorf Centrifuge 5810 and the supernatant removed by decanting. The pulp was resuspended in 8 mL deionized water and filtered through a nylon filter (diameter 20 mm) under suction. The formed paper pads were placed on a metal plate, covered with 3 layers of filter paper and pressed in a two step procedure using a Labtech automatic sheet press. Press step 1: 0.4 MPa for 5.5 minutes and press step 2: 0.4 MPa for 3 minutes. The pads were dried over night at room temperature. Brightness were determined using a Macbeth Color-Eye 7000 Remissions spectrophotometer, measuring two times on each pad at 460 nm (on each side).

TABLE 6

Brightness of oxygenated eucalyptus kraft pulp after treatment with CiP and 0.5 mM violuric acid at different incubation times.

| Conditions | Time (min) | Brightness (460 nm) |
|---|---|---|
| Raw pulp | — | 62.0 |
| Blank | 15 | 66.9 |
|  | 60 | 67.0 |
|  | 240 | 68.3 |
| 0.3 µg CiP protein/ml + 0.5 mM violuric acid + 2 mM $H_2O_2$ + 0.1 g Neodol 25-3/L | 15 | 70.9 |
|  | 60 | 72.3 |
|  | 240 | 74.2 |

A very good correlation between incubation time during peroxidase/violuric acid treatment and brightness was observed.

Example 7

Bleaching of Unbleached and Oxygen Pre-Bleached Eucalyptus with Royal Palm Tree Peroxidases and Violuric Acid—Enzyme Dosage Profiles Unbleached eucalyptus Kraft pulp sampled before oxygenation and oxygen pre-bleached eucalyptus Kraft pulp were treated with royal palm tree peroxidase (RPP; SEQ ID NO:4) at different dosage levels and 0.5 mM violuric acid (VA). The standard laboratory protocol for the mini assay was applied. The pulps were hydrated in 50 mM acetate buffer pH 4.0 for 30 minutes at room temperature (no stirring).
Conditions:
Different dosage levels of RPP enzyme protein/ml as indicated in Table 7
0.5 mM violuric acid (VA; Fluka 95120)
2×1 mM hydrogen peroxide ($H_2O_2$) added at time 0 min and 30 min.
0.1 g/L Neodol 25-3 (surfactant);
70° C.;
pH 4.0

The brightness values were based on double determinations. A stock solution of 20 mM violuric acid was prepared in de-ionized water.

TABLE 7

Brightness of unbleached and oxygen pre-bleached eucalyptus Kraft pulp after treatment with RPP and 0.5 mM violuric acid followed by alkaline extraction.

| Treatment | Brightness | |
|---|---|---|
| | Unbleached Eucalyptus | Oxygen pre-bleached Eucalyptus |
| Blank + $H_2O_2$ + surfactant | 50.3 | 58.5 |
| Blank + VA + $H_2O_2$ + surfactant | 50.1 | 58.6 |
| 0.00013 mg enzyme protein/ml + VA + $H_2O_2$ + surfactant | 48.4 | 57.6 |
| 0.00063 mg enzyme protein/ml + VA + $H_2O_2$ + surfactant | 49.4 | 59.4 |
| 0.0016 mg enzyme protein/ml + VA + $H_2O_2$ + surfactant | 52.4 | 62.9 |
| 0.0032 mg enzyme protein/ml + VA + $H_2O_2$ + surfactant | 54.5 | 65.8 |
| 0.0063 mg enzyme protein/ml + VA + $H_2O_2$ + surfactant | 54.9 | 67.1 |
| 0.019 mg enzyme protein/ml + VA + $H_2O_2$ + surfactant | 57.6 | 68.0 |
| 0.050 mg enzyme protein/ml + VA + $H_2O_2$ + surfactant | 58.8 | 68.3 |

The RPP peroxidase works well on both unbleached and oxygen pre-bleached eucalyptus pulp.

Example 8

Bleaching of Unbleached and Oxygen Pre-Bleached Eucalyptus with Soybean Peroxidases and Violuric Acid—Enzyme Dosage Profiles Unbleached eucalyptus Kraft pulp sampled before oxygenation and oxygen pre-bleached eucalyptus Kraft pulp were treated with soybean peroxidase (SBP; SEQ ID NO:3) at different dosage levels and 0.5 mM violuric acid (VA). The standard laboratory protocol for the mini assay was applied. The pulps were hydrated in 50 mM acetate buffer pH 4.0 for 30 minutes at room temperature (no stirring).
Conditions:
Different dosage levels of SBP enzyme protein/ml as indicated in Table 8
0.5 mM violuric acid (VA; Fluka 95120)
2×1 mM hydrogen peroxide added at time 0 min and 30 min.
0.1 g/L Neodol 25-3 (surfactant);
70° C.;
pH 4.0

The brightness values were based on double determinations. A stock solution of 20 mM violuric acid was prepared in de-ionized water.

TABLE 8

Brightness of unbleached and oxygen pre-bleached eucalyptus Kraft pulp after treatment with SBP and 0.5 mM violuric acid followed by alkaline extraction.

| Treatment | Brightness | |
|---|---|---|
| | Unbleached Eucalyptus | Oxygen pre-bleached Eucalyptus |
| Blank + $H_2O_2$ + surfactant | 50.3 | 58.5 |
| Blank + VA + $H_2O_2$ + surfactant | 50.1 | 58.6 |
| 0.000065 mg enzyme protein/ml + VA + $H_2O_2$ + surfactant | 50.1 | 59.3 |
| 0.00033 mg enzyme protein/ml + VA + $H_2O_2$ + surfactant | 52.6 | 63.6 |
| 0.00082 mg enzyme protein/ml + VA + $H_2O_2$ + surfactant | 54.3 | 65.8 |
| 0.0016 mg enzyme protein/ml + VA + $H_2O_2$ + surfactant | 56.6 | 66.2 |
| 0.0033 mg enzyme protein/ml + VA + $H_2O_2$ + surfactant | 57.4 | 66.9 |
| 0.0098 mg enzyme protein/ml + VA + $H_2O_2$ + surfactant | 57.1 | 68.1 |
| 0.026 mg enzyme protein/ml + VA + $H_2O_2$ + surfactant | 57.7 | 68.6 |

The SBP enzyme works well on both unbleached and oxygen pre-bleached eucalyptus pulp.

Example 9

Bleaching of Oxygen Pre-Bleached Eucalyptus with Royal Palm Tree Peroxidase and Violuric Acid—Temperature and pH Influence on Activity Oxygen pre-bleached eucalyptus Kraft pulp were treated with royal palm tree peroxidase (RPP; SEQ ID NO:4) at fixed dosage level and 0.5 mM violuric acid (VA). The standard laboratory protocol for the mini assay was applied. The pulps were hydrated in 50 mM acetate buffer pH 4.0 for 30 minutes at room temperature (no stirring).
Conditions:
0.018 mg RPP enzyme protein/ml or no enzyme for Blank treatment
0.5 mM violuric acid (VA; Fluke 95120) or no VA for Blank treatment.
2×1 mM hydrogen peroxide added at time 0 min and 30 min.
0.1 g/L Neodol 25-3 (surfactant);
Temperatures: 66° C.; 75° C.; 80° C.; 83° C.; and 86° C.
pH: 3.5; 4.0; and 5.0

The brightness values were based on double determinations. A stock solution of 20 mM violuric acid was prepared in de-ionized water.

TABLE 9

Brightness of oxygen pre-bleached eucalyptus Kraft pulp after Blank treatment at different pH and Temp followed by alkaline extraction.

| Temp/pH | 3.0 | 3.5 | 4.0 | 5.0 |
|---|---|---|---|---|
| 66 | 68.3 | 67.0 | 67.2 | 64.8 |
| 75 | 71.8 | 68.9 | 70.4 | 67.1 |
| 80 | 67.4 | 67.2 | 67.4 | 68.0 |
| 83 | 72.4 | 70.6 | 72.1 | 69.5 |
| 86 | 69.6 | 67.3 | 66.1 | 64.1 |
| 90 | 71.1 | 70.4 | 71.6 | 69.1 |

TABLE 10

Brightness of oxygen pre-bleached eucalyptus Kraft pulp after peroxidase + VA treatment at different pH and Temp followed by alkaline extraction.

| Temp/pH | 3.0 | 3.5 | 4.0 | 5.0 |
|---|---|---|---|---|
| 66 | 76.0 | 75.8 | 76.4 | 74.0 |
| 75 | 71.6 | 75.5 | 74.6 | 70.6 |
| 80 | 66.2 | 66.2 | 74.9 | 73.9 |
| 83 | 71.0 | 70.3 | 74.3 | 74.4 |
| 86 | 67.3 | 65.3 | 66.7 | 66.8 |
| 90 | 70.1 | 67.8 | 65.1 | 68.3 |

TABLE 11

Delta brightness of oxygen pre-bleached eucalyptus Kraft pulp after peroxidase + VA treatment - Blank treatments at different pH and Temp followed by alkaline extraction. Negative delta brightness is shown as zero.

| Temp/pH | 3.0 | 3.5 | 4.0 | 5.0 |
|---|---|---|---|---|
| 66 | 7.7 | 8.8 | 9.2 | 9.2 |
| 75 | 0 | 6.6 | 4.2 | 3.5 |
| 80 | 0 | 0 | 7.5 | 5.9 |
| 83 | 0 | 0 | 2.3 | 4.9 |
| 86 | 0 | 0 | 0.6 | 2.7 |
| 90 | 0 | 0 | 0 | 0 |

Example 10

Bleaching of Oxygen Pre-Bleached Eucalyptus with Soy Bean Peroxidase and Violuric Acid—pH Influence on Activity at 85° C.

Oxygen pre-bleached eucalyptus Kraft pulp were treated with soy bean peroxidase (SBP; SEQ ID NO:3) at fixed dosage level and 1.0 mM violuric acid (VA). The standard laboratory protocol for the mini assay was applied, but the concentrations during the alkaline extraction was modified and followed the below mentioned conditions. The pulps were hydrated for 30 minutes at room temperature (no stirring) in 50 mM acetate buffer for pH levels ranging from 4-5, phosphate buffers at pH ranging from 6-7 and the lower pH values at 3-3.5 was obtained by direct adjustment with $H_2SO_4$.
Conditions:
0.021 mg SBP enzyme protein/ml or no enzyme for Blank treatment
0.5 mM violuric acid (VA; Fluka 95120) or no VA for Blank treatment.
2×2 mM hydrogen peroxide added at time 0 min and 30 min.
0.1 g/L Neodol 25-3 (surfactant);
Temperature: 85° C.
pH: 3.5; 4.0; 4.5; 5.0; 6.0; and 7.0
Alkaline extraction, Ep conditions:
0.05 g/L $MgSO_4$
1.1 g/L NaOH
0.9 g/L $H_2O_2$
90 min
85° C.

The brightness values were based on double determinations. A stock solution of 20 mM violuric acid was prepared in de-ionized water.

TABLE 12

Brightness of oxygen pre-bleached eucalyptus Kraft pulp after treatment at different pH followed by alkaline extraction.

| | Brightness | | | | | | |
|---|---|---|---|---|---|---|---|
| Treatment | pH 3.0 | pH 3.5 | pH 4.0 | pH 4.5 | pH 5.0 | pH 6.0 | pH 7.0 |
| Blank + surfactant | 67.7 | 68.5 | 66.3 | 67.3 | 67.1 | 65.5 | 64.4 |
| Blank + $H_2O_2$ + surfactant | 71.4 | 70.2 | 70.1 | 70.6 | 68.8 | 66.9 | 65.6 |
| SBP + VA + $H_2O_2$ + surfactant | 69.9 | 72.5 | 75.8 | 75.8 | 73.4 | 68.1 | 66.0 |

The soy bean peroxidase (SBP)+violuric acid (VA) system shows activity over a broad pH range at 85° C.

Example 11

Bleaching of Oxygen Pre-Bleached Eucalyptus with Soy Bean Peroxidase and Violuric Acid—pH Influence on Activity at 70° C.

Oxygen pre-bleached eucalyptus Kraft pulp were treated with soy bean peroxidase (SBP; SEQ ID NO:3) at fixed dosage level and 0.5 mM violuric acid (VA). The standard laboratory protocol for the mini assay was applied, but the concentrations during the alkaline extraction was modified and followed the below mentioned conditions. The pulps were hydrated for 30 minutes at room temperature (no stirring) in 50 mM acetate buffer for pH levels ranging from 4-5, phosphate buffer at pH 6 and the lower pH values at 3-3.5 was obtained by direct adjustment with $H_2SO_4$.
Conditions:
0.001 mg SBP enzyme protein/ml or no enzyme for Blank treatment
0.5 mM violuric acid (VA; Fluka 95120) or no VA for Blank treatment. A stock solution of 20 mM violuric acid was prepared in de-ionized water.
2×2 mM hydrogen peroxide added at time 0 min and 30 min.
0.1 g/L Neodol 25-3 (surfactant);
Temperature: 70° C.
pH: 3.0; 3.5; 4.0; 4.5; 5.0; and 6.0
Alkaline extraction, Ep conditions:
0.05 g/L $MgSO_4$
1.1 g/L NaOH
0.9 g/L $H_2O_2$
90 min
85° C.

The brightness values were based on double determinations. A stock solution of 20 mM violuric acid was prepared in de-ionized water.

TABLE 13

Brightness of oxygen pre-bleached eucalyptus Kraft pulp after treatment at different pH followed by alkaline extraction.

| | Brightness | | | | | |
|---|---|---|---|---|---|---|
| Treatment | pH 3.0 | pH 3.5 | pH 4.0 | pH 4.5 | pH 5.0 | pH 6.0 |
| Blank + surfactant | 63.5 | 65.3 | 64.6 | 64.5 | 65.0 | 64.9 |
| SBP + VA + $H_2O_2$ + surfactant | 64.5 | 65.9 | 72.1 | 72.4 | 73.5 | 65.7 |

The soy bean peroxidase (SBP)+violuric acid (VA) system works well over a broad pH range at 70° C.

Example 12

Bleaching of Oxygen Pre-Bleached Eucalyptus with Soy Bean Peroxidase and Violuric Acid at Different Temperatures Oxygenated eucalyptus pulp was treated with soy bean peroxidase (SBP; SEQ ID NO:3) at fixed dosage level of 0.011 mg protein/L and 0.5 mM violuric acid (VA). (VA; Fluka 95120). Hydrogen peroxide ($H_2O_2$; Merck, Perhydrol 30%) was dosed at 4 mM concentration level. All treatments included 0.1 g/L of Neodol 25-3.

The following procedure was applied:

5 g dry oxygenated eucalyptus pulp was weighed into a Stomacher plastic bag (BA6040, Seward). 22.5 ml 100 mM acetate buffer pH 4.5 was added to the pulp and the stomacher bag was sealed. The pulp was hydrated for 30 minutes at 60° C. in a water bath. De-ionized water, enzyme, mediator, surfactant and H2O2 were added to the pulp (in the stated order) and mixed by hand between each ingredient. The amount of water was adjusted to give a final volume of 50 ml. The samples were incubated for 180 min at 60° C., 70° C. or 80° C. and the pulp was drained by filtration (vacuum) using a glass funnel with a binding clamp polyester. The drained pulp was washed twice with 100 ml of de-ionized water and drained. The pulp was further given an alkaline extraction including peroxide (Ep) after which it was washed and sheets formed for brightness measurements. The following procedure was applied:

The drained pulp was transferred into a plastic bag and extraction liquids added resulting in $MgSO_4$ 0.5 kg/ton dry pulp, NaOH 10 kg/ton dry pulp and $H_2O_2$ 8 kg/ton dry pulp. Total volume of 50 ml. The bags were placed in water bath at 85° C. for 90 min. After extraction liquids were drained and the drained pulp was washed twice with 100 ml of de-ionized water and drained.

The pad is further pressed 5:30 min with blotting paper. The pressed pulp is transferred to Tappi disintegrator and 2 L deionized water is added and disintegration is carried out for 300 revolutions another 0.5 L of water is added and 1 L of the pulp suspension is used for preparing a sheet in a semiautomatic sheet former. The formed paper sheets were placed on a metal plate, covered with 3 layers of filter paper and pressed in a two step procedure using a Labtech automatic sheet press. Press step 1: 0.4 MPa for 5.5 minutes and press step 2: 0.4 MPa for 3 minutes. The pads were dried over night at room temperature. Brightness was determined using a Macbeth Color-Eye 7000 Remissions spectrophotometer, measuring five times on each sheet at 460 nm.

TABLE 14

Brightness of oxygenated eucalyptus Kraft pulp after treatment with SBP + VA at different temperatures followed by alkaline extraction.

| | Brightness | | |
|---|---|---|---|
| Conditions | Temp: 60° C. | Temp: 70° C. | Temp: 80° C. |
| Blank + surfactant | 69.1 | 70.0 | 69.3 |
| SBP + VA + $H_2O_2$ + surfactant | 73.6 | 72.9 | 74.0 |

The soy bean peroxidase (SBP)+violuric acid (VA) system works fine at all three temperatures.

Example 13

Bleaching of Unbleached Eucalyptus with Soybean Peroxidase or Royal Palm Peroxidase and Violuric Acid—Enzyme Dosage Profiles at Different Hydrogen Peroxide Concentrations Unbleached eucalyptus Kraft pulp were treated with soybean peroxidase (SBP; SEQ ID NO:3) or royal palm tree peroxidase (RPP; SEQ ID NO:4) at different dosage levels and 0.5 mM violuric acid (VA). The standard laboratory protocol for the mini assay was applied. The pulps were hydrated in 50 mM acetate buffer pH 4.0 for 30 minutes at room temperature (no stirring).

Conditions:

Different dosage levels of SBP or RPP enzyme protein/ml as indicated in Tables 15 and 16;

0.5 mM violuric acid (VA; Fluka 95120);

2×1; 2×2; 2×3; or 2×5 mM hydrogen peroxide added at time 0 min and 30 min.;

0.1 g/L Neodol 25-3 (surfactant);

70° C.;

pH 4.0.

The brightness values were based on double determinations. A stock solution of 10 mM violuric acid was prepared in de-ionized water.

TABLE 15

Brightness of unbleached eucalyptus Kraft pulp after treatment with SBP and 0.5 mM violuric acid at different hydrogen peroxide concentrations, followed by alkaline extraction.

| | Brightness | | | |
|---|---|---|---|---|
| Treatment with SBP | $H_2O_2$ 2 mM | $H_2O_2$ 4 mM | $H_2O_2$ 6 mM | $H_2O_2$ 10 mM |
| Blank + $H_2O_2$ + surfactant | 49.2 | 48.1 | 47.9 | 49.6 |
| 0.00082 mg enzyme protein/ml + VA + $H_2O_2$ + surfactant | 55.0 | 55.0 | 53.8 | 52.7 |
| 0.0033 mg enzyme protein/ml + VA + $H_2O_2$ + surfactant | 57.0 | 58.5 | 58.6 | 58.2 |
| 0.0098 mg enzyme protein/ml + VA + $H_2O_2$ + surfactant | 58.7 | 58.8 | 59.4 | 59.8 |

The SBP peroxidase works fine at all the different hydrogen peroxide concentrations

TABLE 16

Brightness of unbleached eucalyptus Kraft pulp after treatment with RPP and 0.5 mM violuric acid at different hydrogen peroxide concentrations, followed by alkaline extraction.

| | Brightness | | | |
|---|---|---|---|---|
| Treatment with RPP | $H_2O_2$ 2 mM | $H_2O_2$ 4 mM | $H_2O_2$ 6 mM | $H_2O_2$ 10 mM |
| Blank + $H_2O_2$ + surfactant | 47.7 | 48.1 | 48.0 | 49.1 |
| 0.0063 mg enzyme protein/ml + VA + $H_2O_2$ + surfactant | 55.6 | 54.7 | 55.0 | 53.7 |
| 0.0189 mg enzyme protein/ml + VA + $H_2O_2$ + surfactant | 58.1 | 57.4 | 57.3 | 56.4 |

The RPP peroxidase works fine at all the different hydrogen peroxide concentrations

Example 14

Bleaching of Oxygen Pre-Bleached Eucalyptus with Soy Bean Peroxidase and Violuric Acid at Different Mediator Concentrations Oxygenated eucalyptus pulp was treated with soy bean peroxidase (SBP; SEQ ID NO:3) at fixed dosage level of 0.001 or 0.005 mg protein/L and 0.5 mM or 1.0 mM violuric acid (VA). (VA; Fluka 95120). Traditional hydrogen peroxide ($H_2O_2$; Merck, Perhydrol 30%) was dosed at 4 mM concentration level. All treatments included 0.1 g/L of Neodol 25-3.

The following procedure was applied:

5 g dry oxygenated eucalyptus pulp was weighed into a Stomacher plastic bag (BA6040, Seward). 22.5 ml 100 mM acetate buffer pH 4.5 was added to the pulp and the stomacher bag was sealed. The pulp was hydrated for 30 minutes at 70° C. in a water bath. De-ionized water, enzyme, mediator, surfactant and $H_2O_2$ were added to the pulp (in the stated order) and mixed by hand between each ingredient. The amount of water was adjusted to give a final volume of 50 ml. The samples were incubated for 180 min at 70° C. and the pulp was drained by filtration (vacuum) using a glass funnel with a binding clamp polyester. The drained pulp was washed twice with 100 ml of de-ionized water and drained.

The pulp was further given an alkaline extraction including peroxide (Ep) after which it was washed and sheets formed for brightness measurements. The following procedure was applied:

The drained pulp was transferred into a plastic bag and extraction liquids added resulting in $MgSO_4$ 0.5 kg/ton dry pulp, NaOH 10 kg/ton dry pulp and $H_2O_2$ 8 kg/ton dry pulp. Total volume was 50 ml. The bags were placed in water bath at 85° C. for 90 min. After extraction liquids were drained and the drained pulp was washed twice with 100 ml of de-ionized water and drained. The pad is further pressed 5:30 min with blotting paper. The pressed pulp is transferred to Tappi disintegrator and 2 L deionized water is added and disintegration is carried out for 300 revolutions another 0.5 L of water is added and 1 L of the pulp suspension is used for preparing a sheet in a semiautomatic sheet former. The formed paper sheets were placed on a metal plate, covered with 3 layers of filter paper and pressed in a two step procedure using a Labtech automatic sheet press. Press step 1: 0.4 MPa for 5.5 minutes and press step 2: 0.4 MPa for 3 minutes. The pads were dried over night at room temperature. Brightness was determined using a Macbeth Color-Eye 7000 Remissions spectrophotometer, measuring five times on each sheet at 460 nm.

TABLE 17

Brightness of oxygenated eucalyptus Kraft pulp after treatment with SBP + VA at different temperatures, followed by alkaline extraction.

| Conditions | Brightness |
| --- | --- |
| Blank + surfactant | 70.5 |
| Blank + $H_2O_2$ + surfactant | 71.0 |
| 0.001 mg enzyme protein/ml + 0.5 mM VA + $H_2O_2$ + surfactant | 73.4 |
| 0.005 mg enzyme protein/ml + 0.5 mM VA + $H_2O_2$ + surfactant | 73.0 |
| 0.001 mg enzyme protein/ml + 1.0 mM VA + $H_2O_2$ + surfactant | 75.5 |
| 0.005 mg enzyme protein/ml + 1.0 mM VA + $H_2O_2$ + surfactant | 75.1 |

The invention claimed is:

1. A method for bleaching pulp, comprising contacting the pulp in an aqueous solution at from about pH 2 to about pH 7 with a plant peroxidase, a source of hydrogen peroxide, and a mediator having the chemical structure:

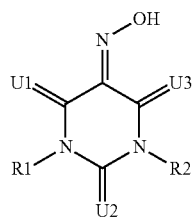

wherein U1, U2 and U3 are identical or different, and are O, S or NOH; and R1 and R2 are identical or different, and are hydrogen, hydroxyl, formyl, carbamoyl or sulfono radical, ester or salt of the sulfono radical, sulfamoyl, nitro, nitroso, amino, cyano, phenyl, benzyl $C_1$-$C_4$-alkyl, $C_1$-$C_4$-alkoxy, $C_1$-$C_4$-carbonyl, or carbonyl-$C_1$-$C_4$-alkyl, wherein the plant peroxidase comprises or consists of an amino acid sequence which has at least 95% sequence identity to SEQ ID NO:3, or SEQ ID NO:4.

2. The method of claim 1, wherein U1, U2 and U3 are identical or different, and are O or S; and R1 and R2 are identical or different, and are hydrogen, hydroxyl, methyl, ethyl, phenyl, benzyl, formyl, amino, cyano, nitroso, methoxy and/or ethoxy.

3. The method of claim 1, wherein U1, U2 and U3 are O; and R1 and R2 are identical or different, and are hydrogen, hydroxyl, methyl, ethyl, phenyl, benzyl, formyl, amino, cyano, nitroso, methoxy and/or ethoxy.

4. The method of claim 1, wherein the mediator is selected from 1-methylvioluric acid, 1,3-dimethylvioluric acid, thiovioluric acid, violuric acid, and esters, ethers or salts thereof.

5. The method of claim 4, wherein the mediator is violuric acid, or a salt thereof.

6. The method of claim 1, wherein the pulp is wood pulp.

7. The method of claim 1, wherein the aqueous solution has a pH of from about 2.5 to about 6.

8. The method of claim 1, wherein the plant peroxidase comprises or consists of an amino acid sequence which has at least 99% sequence identity to SEQ ID NO:3, or SEQ ID NO:4.

9. The method of claim 1, wherein the plant peroxidase consists of an amino acid sequence selected from the group consisting of SEQ ID NO:3, and SEQ ID NO:4.

10. The method of claim 1, which further comprises a step of alkaline peroxide bleaching.

11. A method for bleaching pulp, comprising contacting the pulp in an aqueous solution at from about pH 2 to about pH 7 with a soybean peroxidase, a source of hydrogen peroxide, and a mediator having the chemical structure:

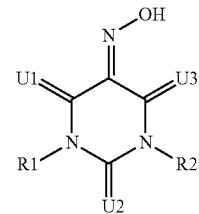

wherein U1, U2 and U3 are identical or different, and are O, S or NOH; and R1 and R2 are identical or different, and are hydrogen, hydroxyl, formyl, carbamoyl or sulfono radical, ester or salt of the sulfono radical, sulfamoyl, nitro, nitroso, amino, cyano, phenyl, benzyl $C_1$-$C_4$-alkyl, $C_1$-$C_4$-alkoxy, $C_1$-$C_4$-carbonyl, or carbonyl-$C_1$-$C_4$-alkyl, wherein the soybean peroxidase comprises or consists of an amino acid sequence which has at least 95% sequence identity to SEQ ID NO:3.

12. The method of claim 11, wherein the mediator is violuric acid, or a salt thereof.

13. The method of claim 11, wherein the peroxidase comprises or consists of the amino acid sequence of SEQ ID NO:3.

* * * * *

SEQUENCE LISTING

```
<160> NUMBER OF SEQ ID NOS: 4

<210> SEQ ID NO 1
<211> LENGTH: 343
<212> TYPE: PRT
<213> ORGANISM: Coprinus cinereus

<400> SEQUENCE: 1

Gln Gly Pro Gly Gly Gly Gly Ser Val Thr Cys Pro Gly Gly Gln Ser
1               5                   10                  15

Thr Ser Asn Ser Gln Cys Cys Val Trp Phe Asp Val Leu Asp Asp Leu
            20                  25                  30

Gln Thr Asn Phe Tyr Gln Gly Ser Lys Cys Glu Ser Pro Val Arg Lys
        35                  40                  45

Ile Leu Arg Ile Val Phe His Asp Ala Ile Gly Phe Ser Pro Ala Leu
    50                  55                  60

Thr Ala Ala Gly Gln Phe Gly Gly Gly Gly Ala Asp Gly Ser Ile Ile
65                  70                  75                  80

Ala His Ser Asn Ile Glu Leu Ala Phe Pro Ala Asn Gly Gly Leu Thr
                85                  90                  95

Asp Thr Val Glu Ala Leu Arg Ala Val Gly Ile Asn His Gly Val Ser
            100                 105                 110

Phe Gly Asp Leu Ile Gln Phe Ala Thr Ala Val Gly Met Ser Asn Cys
        115                 120                 125

Pro Gly Ser Pro Arg Leu Glu Phe Leu Thr Gly Arg Ser Asn Ser Ser
    130                 135                 140

Gln Pro Ser Pro Pro Ser Leu Ile Pro Gly Pro Gly Asn Thr Val Thr
145                 150                 155                 160
```

```
Ala Ile Leu Asp Arg Met Gly Asp Ala Gly Phe Ser Pro Asp Glu Val
            165                 170                 175

Val Asp Leu Leu Ala Ala His Ser Leu Ala Ser Gln Glu Gly Leu Asn
                180                 185                 190

Ser Ala Ile Phe Arg Ser Pro Leu Asp Ser Thr Pro Gln Val Phe Asp
            195                 200                 205

Thr Gln Phe Tyr Ile Glu Thr Leu Leu Lys Gly Thr Thr Gln Pro Gly
        210                 215                 220

Pro Ser Leu Gly Phe Ala Glu Glu Leu Ser Pro Phe Pro Gly Glu Phe
225                 230                 235                 240

Arg Met Arg Ser Asp Ala Leu Leu Ala Arg Asp Ser Arg Thr Ala Cys
                245                 250                 255

Arg Trp Gln Ser Met Thr Ser Ser Asn Glu Val Met Gly Gln Arg Tyr
                260                 265                 270

Arg Ala Ala Met Ala Lys Met Ser Val Leu Gly Phe Asp Arg Asn Ala
            275                 280                 285

Leu Thr Asp Cys Ser Asp Val Ile Pro Ser Ala Val Ser Asn Asn Ala
        290                 295                 300

Ala Pro Val Ile Pro Gly Gly Leu Thr Val Asp Ile Glu Val Ser
305                 310                 315                 320

Cys Pro Ser Glu Pro Phe Pro Glu Ile Ala Thr Ala Ser Gly Pro Leu
                325                 330                 335

Pro Ser Leu Ala Pro Ala Pro
            340

<210> SEQ ID NO 2
<211> LENGTH: 305
<212> TYPE: PRT
<213> ORGANISM: Armoracia rusticana

<400> SEQUENCE: 2

Gln Leu Asn Ala Thr Phe Tyr Ser Gly Thr Cys Pro Asn Ala Ser Ala
1               5                   10                  15

Ile Val Arg Ser Thr Ile Gln Gln Ala Phe Gln Ser Asp Thr Arg Ile
            20                  25                  30

Gly Ala Ser Leu Ile Arg Leu His Phe His Asp Cys Phe Val Asp Gly
        35                  40                  45

Cys Asp Ala Ser Ile Leu Leu Asp Asp Ser Gly Ser Ile Gln Ser Glu
    50                  55                  60

Lys Asn Ala Gly Pro Asn Ala Asn Ser Ala Arg Gly Phe Asn Val Val
65                  70                  75                  80

Asp Asn Ile Lys Thr Ala Leu Glu Asn Thr Cys Pro Gly Val Val Ser
                85                  90                  95

Cys Ser Asp Ile Leu Ala Leu Ala Ser Glu Ala Ser Val Ser Leu Thr
            100                 105                 110

Gly Gly Pro Ser Trp Thr Val Leu Leu Gly Arg Arg Asp Ser Leu Thr
        115                 120                 125

Ala Asn Leu Ala Gly Ala Asn Ser Ala Ile Pro Ser Pro Phe Glu Gly
    130                 135                 140

Leu Ser Asn Ile Thr Ser Lys Phe Ser Ala Val Gly Leu Asn Thr Asn
145                 150                 155                 160

Asp Leu Val Ala Leu Ser Gly Ala His Thr Phe Gly Arg Ala Arg Cys
                165                 170                 175

Gly Val Phe Asn Asn Arg Leu Phe Asn Phe Ser Gly Thr Asn Gly Pro
```

```
            180                 185                 190
Asp Pro Thr Leu Asn Ser Thr Leu Leu Ser Ser Leu Gln Gln Leu Cys
        195                 200                 205

Pro Gln Asn Gly Ser Ala Ser Thr Ile Thr Asn Leu Asp Leu Ser Thr
    210                 215                 220

Pro Asp Ala Phe Asp Asn Asn Tyr Phe Ala Asn Leu Gln Ser Asn Asn
225                 230                 235                 240

Gly Leu Leu Gln Ser Asp Gln Glu Leu Phe Ser Thr Leu Gly Ser Ala
                245                 250                 255

Thr Ile Ala Val Val Thr Ser Phe Ala Ser Asn Gln Thr Leu Phe Phe
            260                 265                 270

Gln Ala Phe Ala Gln Ser Met Ile Asn Met Gly Asn Ile Ser Pro Leu
        275                 280                 285

Thr Gly Ser Asn Gly Glu Ile Arg Leu Asp Cys Lys Lys Val Asp Gly
    290                 295                 300

Ser
305

<210> SEQ ID NO 3
<211> LENGTH: 327
<212> TYPE: PRT
<213> ORGANISM: Glycine max

<400> SEQUENCE: 3

Gln Leu Asp Pro Ser Phe Tyr Arg Asp Thr Cys Pro Arg Val His Ser
1               5                   10                  15

Ile Val Arg Glu Val Val Arg Asn Val Ser Lys Lys Asp Pro Arg Met
            20                  25                  30

Leu Ala Ser Leu Ile Arg Leu His Phe His Asp Cys Phe Val Gln Gly
        35                  40                  45

Cys Asp Ala Ser Val Leu Leu Asn Asn Thr Ala Thr Ile Glu Ser Glu
    50                  55                  60

Gln Gln Ala Leu Pro Asn Asn Ser Leu Arg Gly Leu Asp Val Val
65                  70                  75                  80

Asn Tyr Ile Lys Thr Ala Val Glu Lys Ala Cys Pro Gly Val Val Ser
                85                  90                  95

Cys Ala Asp Ile Leu Thr Leu Ala Ser Gln Ile Ser Ser Val Leu Gly
            100                 105                 110

Gly Gly Pro His Trp Lys Val Pro Leu Gly Arg Arg Asp Ser Leu Thr
        115                 120                 125

Ala Asn Arg Asn Leu Ala Asn Gln Asn Leu Pro Ala Pro Phe Phe Asn
    130                 135                 140

Leu Ser Arg Leu Lys Ala Ala Phe Ala Val Gln Gly Leu Asp Thr Thr
145                 150                 155                 160

Asp Leu Val Ala Leu Ser Gly Ala His Thr Phe Gly Arg Ala His Cys
                165                 170                 175

Asn Phe Ile Leu Asp Arg Leu Tyr Asn Phe Ser Gly Thr Gly Lys Pro
            180                 185                 190

Asp Pro Thr Leu Asp Thr Thr Tyr Leu Gln Gln Leu Arg Gln Ile Cys
        195                 200                 205

Pro Asn Gly Gly Pro Asn Asn Leu Val Asn Phe Asp Pro Val Thr Pro
    210                 215                 220

Asp Lys Ile Asp Arg Val Tyr Phe Ser Asn Leu Gln Val Lys Lys Gly
225                 230                 235                 240
```

```
Leu Leu Gln Ser Asp Gln Glu Leu Phe Ser Thr Pro Gly Ala Asp Thr
                245                 250                 255

Ile Pro Ile Val Asn Arg Phe Ser Ser Asp Gln Lys Val Phe Phe Asp
            260                 265                 270

Ala Phe Glu Ala Ser Met Ile Lys Met Gly Asn Ile Gly Val Leu Thr
        275                 280                 285

Gly Lys Lys Gly Glu Ile Arg Lys His Cys Asn Phe Val Asn Lys Lys
    290                 295                 300

Ser Val Glu Val Asp Ile Ala Ser Val Ala Ser Glu Glu Ser Ser Thr
305                 310                 315                 320

Glu Gly Met Val Thr Ser Ile
                325

<210> SEQ ID NO 4
<211> LENGTH: 304
<212> TYPE: PRT
<213> ORGANISM: Roystonea sp.

<400> SEQUENCE: 4

Asp Leu Gln Ile Gly Phe Tyr Asn Thr Ser Cys Pro Thr Ala Glu Ser
1               5                   10                  15

Leu Val Gln Gln Ala Val Ala Ala Phe Ala Asn Asn Ser Gly Ile
            20                  25                  30

Ala Pro Gly Leu Ile Arg Met His Phe His Asp Cys Phe Val Arg Gly
        35                  40                  45

Cys Asp Ala Ser Val Leu Leu Asp Ser Thr Ala Asn Asn Thr Ala Glu
    50                  55                  60

Lys Asp Ala Ile Pro Asn Asn Pro Ser Leu Arg Gly Phe Glu Val Ile
65                  70                  75                  80

Thr Ala Ala Lys Ser Ala Val Glu Ala Ala Cys Pro Gln Thr Val Ser
                85                  90                  95

Cys Ala Asp Ile Leu Ala Phe Ala Ala Arg Asp Ser Ala Asn Leu Ala
            100                 105                 110

Gly Asn Ile Thr Tyr Gln Val Pro Ser Gly Arg Arg Asp Gly Thr Val
        115                 120                 125

Ser Leu Ala Ser Glu Ala Asn Ala Gln Ile Pro Ser Pro Leu Phe Asn
    130                 135                 140

Ala Thr Gln Leu Ile Asn Ser Phe Ala Asn Lys Thr Leu Thr Ala Asp
145                 150                 155                 160

Glu Met Val Thr Leu Ser Gly Ala His Ser Ile Gly Val Ala His Cys
                165                 170                 175

Ser Ser Phe Thr Asn Arg Leu Tyr Asn Phe Asn Ser Gly Ser Gly Ile
            180                 185                 190

Asp Pro Thr Leu Ser Pro Ser Tyr Ala Ala Leu Leu Arg Asn Thr Cys
        195                 200                 205

Pro Ala Asn Ser Thr Arg Phe Thr Pro Ile Thr Val Ser Leu Asp Ile
    210                 215                 220

Ile Thr Pro Ser Val Leu Asp Asn Met Tyr Tyr Thr Gly Val Gln Leu
225                 230                 235                 240

Thr Leu Gly Leu Leu Thr Ser Asp Gln Ala Leu Val Thr Glu Ala Asn
                245                 250                 255
```

```
Leu Ser Ala Ala Val Lys Ala Asn Ala Met Asn Leu Thr Ala Trp Ala
            260                 265                 270

Ser Lys Phe Ala Gln Ala Met Val Lys Met Gly Gln Ile Glu Val Leu
            275                 280                 285

Thr Gly Thr Gln Gly Glu Ile Arg Thr Asn Cys Ser Val Val Asn Ser
            290                 295                 300
```